United States Patent [19]

Danilewicz et al.

[11] Patent Number: 5,036,104

[45] Date of Patent: Jul. 30, 1991

[54] CYCLOALKYL-SUBSTITUTED GLUTARAMIDE DIURETIC AGENTS

[75] Inventors: John C. Danilewicz, Nr. Canterbury; Keith James, Deal, both of England

[73] Assignee: Pfizer Inc., New York, N.Y.

[21] Appl. No.: 538,357

[22] Filed: Jun. 14, 1990

Related U.S. Application Data

[62] Division of Ser. No. 349,025, May 8, 1989, Pat. No. 4,960,792.

[30] Foreign Application Priority Data

May 27, 1988 [GB] United Kingdom ............... 8812597

[51] Int. Cl.$^5$ .................... A61K 31/16; A61K 31/19; A61K 31/215; C07C 271/06

[52] U.S. Cl. .................... 514/513; 514/530; 514/563; 560/27; 560/44; 560/116; 560/118; 562/450; 562/498; 562/500

[58] Field of Search .................... 560/116, 27, 44, 118; 562/500, 450, 498; 514/530, 513, 563

[56] References Cited

FOREIGN PATENT DOCUMENTS 274234 7/1988 European Pat. Off. .

*Primary Examiner*—Johann Richter
*Attorney, Agent, or Firm*—Peter C. Richardson; J. Trevor Lumb; Robert K. Blackwood

[57] ABSTRACT

2-Acylaminoalkyl-3-[1-(carboxycycloalkylcarbamoyl)-cycloalkyl]propanoic acid derivatives (which may also be viewed as glutaramide derivatives) are useful in the treatment of hypertension, heart failure and renal insufficiency, based upon their inhibition of zinc-dependent, neutral endopiptidase.

10 Claims, No Drawings

CYCLOALKYL-SUBSTITUTED GLUTARAMIDE DIURETIC AGENTS

This is a division, of application Ser. No. 07/349,025, filed on May 8, 1989 now U.S. Pat. No. 4,960,792.

BACKGROUND OF THE INVENTION

This invention relates to a series of cycloalkyl-substituted glutaramide derivatives which are diuretic agents having utility in a variety of therapeutic areas including the treatment of various cardiovascular disorders such as hypertension, heart failure and renal insufficiency.

The compounds are inhibitors of the zinc-dependent, neutral endopeptidase E.C.3.4.24.11. This enzyme is involved in the breakdown of several peptide hormones, including atrial natriuretic factor (ANF), which is secreted by the heart and which has potent vasodilatory, diuretic and natriuretic activity. Thus, the compounds of the invention, by inhibiting the neutral endopeptidase E.C.3.4.24.11, can potentiate the biological effects of ANF, and in particular the compounds are diuretic agents having utility in the treatment of a number of disorders, including hypertension, heart failure, angina, renal insufficiency, premenstrual syndrome, cyclical oedema, Menières disease, hyperaldosteronism (primary and secondary) pulmonary oedema, ascites, and hypercalciuria. In addition, because of their ability to potentiate the effects of ANF the compounds have utility in the treatment of glaucoma. As a further result of their ability to inhibit the neutral endopeptidase E.C.3.4.24.11 the compounds of the invention may have activity in other therapeutic areas including for example the treatment of asthma, inflammation, pain, epilepsy, affective disorders, dementia and geriatric confusion, obesity and gastrointestinal disorders (especially diarrhoea and irritable bowel syndrome), the modulation of gastric acid secretion and the treatment of hyperreninaemia and leukemia.

Published European Patent application No. 0274234 of the same assignee discloses structurally related compounds having the same utility.

SUMMARY OF THE INVENTION

The compounds are of the formula:

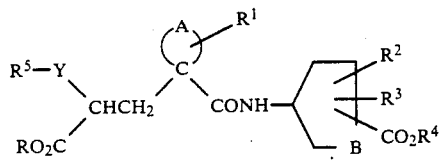

(I)

wherein

A completes a 4 to 7 membered carbocyclic ring which may be saturated or mono-unsaturated and which may optionally be fused to a further saturated or unsaturated 5 or 6 membered carbocyclic ring;

B is $(CH_2)_m$ wherein m is an integer of from 1 to 3;

each of R and $R^4$ is independently H, $C_1-C_6$ alkyl, benzyl or an alternative biolabile ester-forming group;

$R^1$ is H or $C_1-C_4$ alkyl;

$R^2$ and $R^3$ are each independently H, OH, $C_1-C_6$ alkyl or $C_1-C_6$ alkoxy; or $R^2$ and $R^3$ are linked together and are $(CH_2)_r$ wherein r is an integer of from 1 to 4;

Y is an optional alkylene group of from 1 to 6 carbon atoms which may be straight or branched-chain; and $R^5$ is $R^6CONR^9-$, $R^6SO_2NR^9-$, $R^6CO_2-$, $R^6CO-$, $R^6SO_q-$, $R^7NR^9CO-$, $R^7NR^9SO_2-$ or $R^7OCO-$;

wherein $R^6$ is a group of the formula:

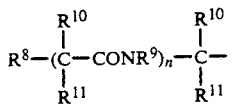

$R^7$ is a group of the formula:

and $R^9$ is H, $C_1-C_6$ alkyl, aryl, $C_3-C_7$ cycloalkyl, heterocyclyl, aryl($C_1-C_6$ alkyl) or heterocyclyl($C_1-C_6$ alkyl);

wherein $R^8$ is $R^9CONR^9-$, $R^9SO_2NR^9-$, $R^{13}R^{14}N-(CH_2)_p-$, or $R^9O-$, wherein each $R^9$ is as previously defined above;

$R^{10}$ and $R^{11}$ are each independently H or $C_1-C_6$ alkyl; or $R^{10}$ is H and $R^{11}$ is $C_1-C_6$ alkyl which is substituted by OH, SH, $SCH_3$, $NH_2$, aryl($C_1-C_6$ alkyl)OCONH—, $NH_2CO-$, $CO_2H$, guanidino, aryl, or heterocyclyl; or the two groups $R^{10}$ and $R^{11}$ are joined together to form, with the carbon atom to which they are attached, a 5 or 6 membered carbocyclic ring which may be saturated or mono-unsaturated and which may optionally be substituted by $C_1-C_4$ alkyl or fused to a further 5 or 6 membered saturated or unsaturated carbocyclic ring;

or $R^{10}$ is H, n is O and $R^8$ and $R^{11}$ are linked to form a 2-(N—$COR^9$-4-aminopyrrolidinyl) group;

$R^{12}$ is $R^{13}R^{14}NCO-$, $R^9OCO-$, $R^9OCH_2-$ or heterocyclyl, wherein $R^9$ is as previously defined above;

$R^{13}$ and $R^{14}$ are each independently H, $C_1-C_6$ alkyl, $C_3-C_7$ cycloalkyl, aryl, aryl($C_1-C_6$ alkyl), $C_2-C_6$ alkoxyalkyl, amino($C_1-C_6$ alkyl), heterocyclyl or heterocyclyl($C_1-C_6$ alkyl); or the two groups $R^{13}$ and $R^{14}$ are taken together to form, with the nitrogen to which they are attached, a pyrrolidinyl, piperidino, morpholino, piperazinyl, N—($C_1-C_4$ alkyl)piperazinyl, pyrrolyl, imidazolyl, pyrazolyl or triazolyl group;

n is 0 or 1;

p is 0 or an integer of from 1 to 6;

and q is 0, 1 or 2;

and pharmaceutically acceptable salts thereof and bioprecursors therefor.

In the above definition, unless otherwise indicated, alkyl groups having three or more carbon atoms may be straight or branched-chain. The term aryl as used herein means an aromatic hydrocarbon group such as phenyl, naphthyl or biphenyl which may optionally be substituted, for example with one or more OH, CN, $CF_3$, $C_1-C_4$ alkyl, $C_1-C_4$ alkoxy, halo, carbamoyl, aminosulphonyl, amino, mono or di($C_1-C_4$ alkyl)amino or ($C_1-C_4$ alkanoyl)amino groups. Halo means fluoro, chloro, bromo or iodo.

The term heterocyclyl means a 5 or 6 membered nitrogen, oxygen or sulphur containing heterocyclic group which, unless otherwise stated, may be saturated or unsaturated and which may optionally include a further oxygen or one to three nitrogen atoms in the ring and which may optionally be benzofused or substituted with for example, one or more halo, $C_1-C_4$ alkyl, hydroxy, carbamoyl, benzyl, oxo, amino or mono or di-($C_1-C_4$ alkyl)amino or ($C_1-C_4$ alkanoyl)amino groups. Particular examples of heterocycles include pyridyl, pyrazinyl, pyrimidinyl, pyridazinyl, pyrrolyl, imidazolyl, pyrazolyl, triazolyl, tetrazolyl, furanyl, tetrahydrofuranyl, tetrahydropyranyl, dioxanyl, thienyl, oxazolyl, isoxazolyl, thiazolyl, indolyl, isoindolinyl, quinolyl, quinoxalinyl, quinazolinyl and benzimidazolyl, each being optionally substituted as previously defined.

The compounds of formula (I) may contain several asymmetric centres and thus they can exist as enantiomers and diastereomers. The invention includes both mixtures and the separated individual isomers. The substituents $R^2$, $R^3$ and $CO_2R^4$ may have cis or trans geometry relative to the amide attachment.

The pharmaceutically acceptable salts of the compounds of formula (I) containing an acidic centre are those formed with bases which form non-toxic salts. Examples include the alkali metal salts such as the sodium, potassium or calcium salts or salts with amines such as diethylamine. Compounds having a basic centre can also form acid addition salts with pharmaceutically acceptable acids. Examples include the hydrochloride hydrobromide, sulphate or bisulphate, phosphate or hydrogen phosphate, acetate, citrate, fumarate, gluconate, lactate, maleate, succinate and tartrate salts.

The term bioprecursor in the above definition means a pharmaceutically acceptable biologically degradable derivative of the compound of formula (I) which, upon administration to an animal or human being, is converted in the body to produce a compound of the formula (I).

A preferred group of compounds of the formula (I) are those wherein A is $(CH_2)_4$, $R^1$ is H and B is $(CH_2)_2$, i.e. compounds of the formula (II) below wherein R, $R^2$, $R^3$, $R^4$, Y and $R^5$ are as previously defined for formula (I):

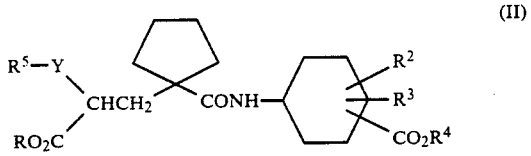
(II)

Also preferred are those compounds of formulae (I) and (II) wherein R and $R^4$ are both H (diacids) as well as biolabile mono and di-ester derivatives thereof wherein one or both of R and $R^4$ is a biolabile ester-forming group.

The term biolabile ester-forming group is well understood in the art as meaning a group which provides an ester which can be readily cleaved in the body to liberate the corresponding diacid of formula (I) wherein R and $R^4$ are both H. A number of such ester groups are well known, for example in the penicillin area or in the case of the ACE-inhibitor antihypertensive agents.

In the case of the compounds of formulae (I) and (II) such biolabile pro-drug esters are particularly advantageous in providing compounds of the formula (I) suitable for oral administration. The suitability of any particular ester-forming group can be assessed by conventional animal or in vitro enzyme hydrolysis studies. Thus, desirably for optimum effect, the ester should only be hydrolysed after absorption, accordingly, the ester should be resistant to hydrolysis before absorption by digestive enzymes but should be readily hydrolyzed by for example, liver enzymes. In this way the active diacid is released into the bloodstream following oral absorption.

In addition to lower alkyl esters (particularly ethyl) and benzyl esters, suitable biolabile esters include alkanoyloxyalkyl esters, including alkyl, cycloalkyl and aryl substituted derivatives thereof, aryloxyalkyl esters, aroyloxyalkyl esters, aralkyloxyalkyl esters, arylesters, aralkylesters, and haloalkyl esters wherein said alkanoyl or alkyl groups have from 1 to 8 carbon atoms and are branched or straight chain and said aryl groups are phenyl, naphthyl or indanyl optionally substituted with one or more $C_1-C_4$ alkyl or $C_1-C_4$ alkoxy groups or halo atoms.

Thus examples of R and $R^4$ when they are biolabile ester-forming groups other than ethyl and benzyl include: 1-(2,2-diethylbutyryloxy)ethyl, 2-ethylpropionyloxymethyl, 1-(2-ethylpropionyloxy)ethyl, 1-(2,4-dimethylbenzoyloxy)ethyl, α-benzoyloxybenzyl, 1-(benzoyloxy)ethyl, 2-methyl-1-propionyloxypropyl, 2,4,6-trimethylbenzoyloxymethyl, 1-(2,4,6-trimethylbenzoyloxy)ethyl, pivaloyloxymethyl, phenethyl, phenpropyl, 2,2,2-trifluoroethyl, 1- or 2-naphthyl, 2,4-dimethylphenyl, 4-t-butylphenyl, 5-(4-methyl-1,3-dioxalynyl-2-onyl)methyl and 5-indanyl.

Particularly preferred biolabile ester-forming groups are ethyl, benzyl, 2,4-dimethylphenyl, 4-t-butylphenyl and 5-indanyl.

Compounds of the formulae (I) and (II) wherein one or both of R and $R^4$ are $C_1-C_6$ alkyl, particularly ethyl, or benzyl, are also active by virtue of their hydrolysis in vivo, and, in addition, are valuable intermediates for the preparation of the diacids wherein R and $R^4$ are both H.

In a further group of preferred compounds of formula (II), R, $R^2$ and $R^4$ are each H. $R^3$ is preferably H or $C_4-C_6$ alkyl especially n-butyl. Particularly preferred are those compounds wherein the carboxy group $COO_2R^4$ is attached at the 3- or 4-position of the cyclohexane ring, most especially those compounds having cis-stereochemistry relative to the amide group.

In one aspect of the invention $R^5$ is $R^6CONR^9$, or $R^7NR^9CO$— wherein $R^9$ is H and $R^6$ is a group of the formula:

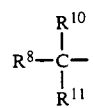

Particularly wherein $R^8$ is ($C_1-C_6$ alkyl)CONH—, arylCONH—, or ($C_1-C_6$ alkyl)$SO_2NH$—, $R^{10}$ is H and $R^{11}$ is $C_1-C_4$ alkyl, benzyl or amino($C_1-C_6$ alkyl).

In a further particular and preferred aspect of the invention Y is methylene and $R^5$ is $N^2$-substituted-L-lysyl-amino, particularly where said substituent is $N^2$-acetyl, $N^2$-benzoyl, $N^2$-naphthoyl or $N^2$-methanesulphonyl; thus preferred compounds are:

2-($N^2$-acetyl-L-lysylaminomethyl)-3-{1-[(cis-4-carboxycyclohexyl)carbamoyl]cyclopentyl}propanoic acid;

2-($N^2$-benzoyl-L-lysylaminomethyl)-3-{1-[cis-4-carboxycyclohexyl)carbamoyl]cyclopentyl}propanoic acid, 2-($N^2$-naphthoyl-L-lysylaminomethyl)-3-{1-[(cis-4-carboxycyclohexyl)carbamoyl]cyclopentyl}propanoic acid, 2-($N^2$-acetyl-L-lysylaminomethyl)-3-{1-[cis-4-carboxy-cis-3-butyl-cyclohexyl)carbamoyl]cyclopentyl} propanoic acid, 2-($N^2$-acetyl-L-lysylaminomethyl)-3-{1-[cis-4-carboxytrans-3-butyl-cyclohexyl)carbamoyl]cyclopentyl} propanoic acid, 2-($N^2$-methanesulphonyl-L-lysylaminomethyl)-3-{1-[cis-4-carboxy-cyclohexyl)carbamoyl]cyclopentyl} propanoic acid, 2-($N^2$-methanesulphonyl-L-lysylaminomethyl)-3-{1-[cis-4-carboxy-cis-3-(3-methylbutyl)cyclohexyl)carbamoyl]cyclopentyl}propanoic acid, and 2-($N^2$-methanesulphonyl-L-lysylaminomethyl)-3-{1-[cis-4-carboxy-cis-3-butyl-cyclohexyl)carbamoyl]cyclopentyl}propanoic acid.

DETAILED DESCRIPTION OF THE INVENTION

The compounds of formula (I) are prepared by a number of different processes according to the invention:

(a) In one process, the compounds of formula (I) wherein $R^5$ is $R^6CONR^9$ are prepared by a process which involves acylating an amine of the formula:

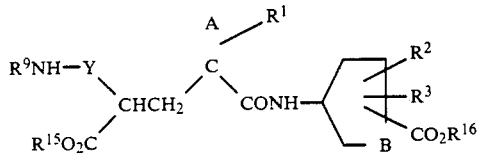

(III)

wherein A, B, Y, $R^1$, $R^2$, $R^3$ and $R^9$ are as previously defined and $R^{15}$ and $R^{16}$ are as previously defined for R and $R^4$ excluding H, or they are conventional carboxylic acid protecting groups; by reaction with an acid of the formula:

$$R^6-CO_2H \qquad (IV)$$

wherein $R^6$ is as previously defined, and wherein any reactive groups therein are optionally protected, to yield a compound of the formula:

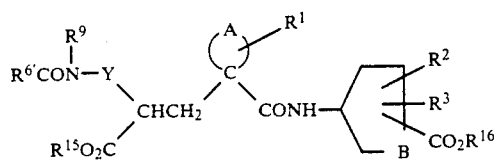

(V)

wherein $R^{6'}$ is as previously defined for $R^6$ with any reactive groups therein optionally protected; and subsequently removing any protecting groups, if present, and, if desired, hydrolysing the ester product to yield the carboxylic acids wherein R and $R^4$ are H.

The reaction of the compounds of formula (III) and (IV) is achieved using conventional amide coupling techniques. Thus in one process the reaction is achieved with the reactants dissolved in an organic solvent, e.g. dichloromethane, using a carbodiimide condensing agent, for example 1-ethyl-3-(3-dimethylaminopropyl)-carbodiimide, or N,N'-dicyclohexylcarbodiimide, advantageously in the presence of 1-hydroxybenzotriazole and an organic base such as N-methylmorpholine. The reaction is generally complete after a period of from 12 to 24 hours at room temperature and the product is then isolated by conventional procedures, i.e. by washing with water or filtration to remove the urea biproduct and evaporation of the solvent. The product may be further purified by crystallisation or chromatography, if necessary. The compounds of formula (V) include compounds of formula (I) wherein R and $R^4$ are $C_1$-$C_6$ alkyl or benzyl.

The diesters of formula (V) may be further reacted to give the monoester or diacid derivatives of formula (I) wherein one or both of R and $R^4$ are H. The conditions used will depend on the precise nature of the groups $R^{15}$ and $R^{16}$ present in the compound of formula (V) and a number of variations are possible. Thus for example when both of $R^{15}$ and $R^{16}$ are benzyl, hydrogenation of the product will yield the diacid of formula (I) wherein R and $R^4$ are both H. Alternatively if $R^{15}$ is benzyl and $R^{16}$ is alkyl, hydrogenation will yield a monoester product. This can then be hydrolysed, if desired, to again yield the diacid product. When one of $R^{15}$ and $R^{16}$ is t-butyl, treatment of the compound of formula (V) with trifluoroacetic acid yields the corresponding acid. The diester product wherein $R^{15}$ and $R^{16}$ are benzyl or lower alkyl can also be treated with trimethylsilyl iodide to produce the dicarboxylic acid product. If some other carboxylic acid protecting group is used for $R^{15}$ or $R^{16}$ then clearly appropriate conditions for its removal must be employed in the final step to give the ester or diacid product of formula (I). In the case where the ring A or the substituent $R^5$ is unsaturated, the deprotection must be effected by non-reductive methods, thus for example if either of R and $R^4$ is benzyl, they may be removed by treatment with trimethylsilyl iodide.

Finally any protecting groups which may be present in $R^{6'}$ are removed by methods appropriate to the particular group used. Thus, for example, if an amino group is present in $R^6$, this may be protected as the benzyloxycarbonylamino group, the benzyloxycarbonyl group being removed in the final step by catalytic hydrogenation.

Compounds of the formula (I) where one or both of R and $R^4$ are biolabile ester forming groups are prepared following similar procedures, starting with a compound of the formula (III) wherein $R^{15}$ and/or $R^{16}$ are biolabile ester forming groups.

In each case the product may be obtained as the free carboxylic acid or it may be neutralised with an appropriate base and isolated in salt form.

The starting cycloalkyl-substituted glutaric acid mono esters of formula III may be prepared by a number of different processes as described in our European patent application no. 0274234.

The acids of formula IV are generally known compounds which are either commercially available or they may be prepared following literature precedents.

(b) In a further process, compounds of the formula (I) wherein $R^5$ in $R^6SO_2NR^9$— are prepared by an entirely analogous procedure by reaction of a sulphonyl halide of formula $R^6SO_2$—hal with the amine of formula (III).

(c) Compounds of the formula (I) wherein $R^5$ is $R^7NR^9CO$— are prepared by reaction of a compound of the formula:

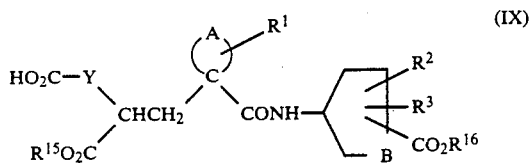

(IX)

wherein A, B, Y, $R^1$, $R^2$, $R^3$, $R^{15}$ and $R^{16}$ are as previously defined, by reaction with an amine of the formula $R^7R^9NH$, followed by removal of any protecting groups which may be present and hydrolysis of the ester product to yield the carboxylic acids wherein R and $R^4$ are H.

The reaction of the compound of formula (IX) and the amine may be achieved using the amide coupling techniques already described under process (a) above. The subsequent steps are also as previously described. The compounds of formula (IX) are prepared following the procedures described in our European patent application no. 0274234 to provide the corresponding benzyl ester (where $R^5$ is $C_6H_5CH_2CO_2$—), catalytic hydrogenation gives the carboxylic acid of formula (IX). The amines of formula $R^7R^9NH$ are generally derived from the naturally occurring amino acids with appropriate protection of reactive side chains.

(d) In a further process compounds of formula (I) wherein $R^5$ is $R^6CONR^9$ or wherein $R^5$ is $R^6CO_2$—, $R^6CO$—, $R^6SO_q$—, $R^7NR^9SO_2$— or $R^7OCO$ are prepared following the synthetic procedure described in our European patent application no. 0274234, i.e. using the following process:

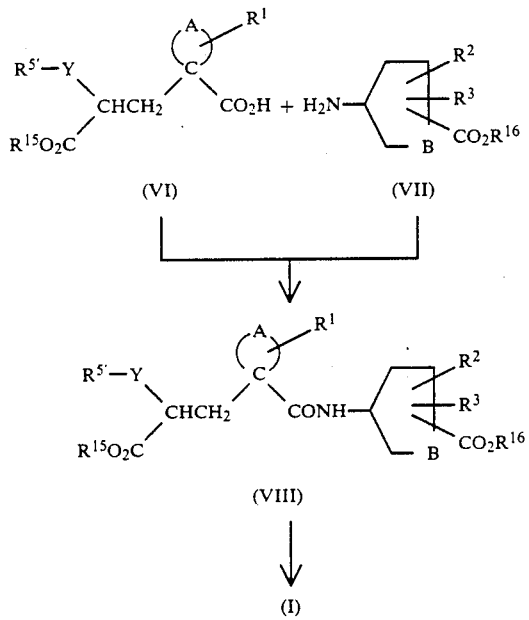

wherein A, B, Y, $R^1$, $R^2$, $R^3$, $R^{15}$ and $R^{16}$ are as previously defined and $R^{5'}$ is as defined by $R^5$ with any reactive groups therein optionally protected.

The protecting and coupling techniques required are as previously described. The compounds of formulae (VI) and (VII) may be prepared following the general procedures described in the above-mentioned European patent application.

As previously mentioned, the compounds of the invention are potent inhibitors of the neutral endopeptidase (E.C.3.4.24.11). This enzyme is involved in the breakdown of a number of peptide hormones and, in particular it is involved in the breakdown of atrial natriuretic factor (ANF). This hormone consists of a family of related natriuretic peptides, secreted by the heart, of which the major circulating form in humans is known to be the 28 amino-acid peptide referred to as α-hANP (see for example G. A. Sagnella and G. A. MacGregor, Nature, 1984, 309, 666 and S. A. Atlas and others, Nature, 1984, 309, 717–725). Thus, the compounds of the invention, by preventing the degradation of ANF, by endopeptidase E.C.3.4.24.11 can potentiate its biological effects and the compounds are thus diuretic and natriuretic agents of utility in a number of disorders as previously described.

Activity against neutral endopeptidase E.C.3.4.24.11 is assessed using a procedure based on the assay described by J. T. Gafford, R. A. Skidgel, E. G. Erdos and L. B. Hersh, Biochemistry, 1983, 32, 3265–3271. The method involves determining the concentration of compound required to reduce by 50% the rate of release of radiolabelled hippuric acid from hippuryl-L-phenylalanyl-L-arginine by a neutral endopeptidase preparation from rat kidney.

The activity of the compounds as diuretic agents is determined by measuring their ability to increase urine output and sodium ion excretion in saline loaded conscious mice. In this test, male mice (Charles River CD1, 22–28 g) are acclimatised and starved overnight in metabowls. The mice are dosed intravenously via the tail vein, with the test compound dissolved in a volume of saline solution equivalent to 2.5% of body weight. Urine samples are collected each hour for two hours in pre-weighed tubes and analysed for electrolyte concentration. Urine volume and sodium ion concentration from the test animals are compared to a control group which received only saline.

For administration to man in the curative or prophylactic treatment of hypertension, congestive heart failure or renal insufficiency, oral dosages of the compounds will generally be in the range of from 4–800 mg daily for an average adult patient (70 kg). Thus for a typical adult patient, individual tablets or capsules contain from 2 to 400 mg of active compound, in a suitable pharmaceutically acceptable vehicle or carrier for administration singly, or in multiple doses, once or several times a day. Dosages for intravenous administration would typically be within the range 1 to 400 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

The compounds may be administered alone but may also be administered together with such other agents as the physician shall direct to optimise control of blood pressure or to treat congestive heart failure, renal insufficiency or other disorders in any particular patient in accordance with established medical practice. Thus the compounds can be co-administered with a variety of cardiovascular agents, for example with an ACE inhibitor such as captopril or enalapril to facilitate the control of blood pressure in treatment of hypertension; or with digitalis, or another cardiac stimulant or with an ACE inhibitor, for the treatment of congestive heart failure. Other possibilities include co-administration with a calcium antagonist (e.g. nifedipine, amlodipine or diltiazem) a beta-blocker (e.g. atenolol) or an alpha-blocker (e.g. prazosin or doxazosin) as shall be determined by the physician as appropriate for the treatment of the particular patient or condition involved.

In addition to the above, the compounds may also be administered in conjunction with exogenous ANF, or a derivative thereof or related peptide or peptide fragment having diuretic/natriuretic activity or with other ANF-gene related peptides (e.g. as described by D. L. Vesely et al, Biochem. Biophys. Res. Comm., 1987, 143, 186).

Thus in a further aspect the invention provides a pharmaceutical composition comprising a compound of the formula (I), or a pharmaceutically acceptable salt thereof or bioprecursor therefor, together with a pharmaceutically acceptable diluent or carrier.

The invention also includes a compounds of the formula (I), or a pharmaceutically acceptable salt thereof or bioprecursor therefor, for use in medicine, particularly for use as a diuretic agent for the treatment of hypertension, congestive heart failure or renal insufficiency in a human being.

The invention further includes the use of a compound of the formula (I) for the manufacture of a medicament for the treatment of hypertension, heart failure, angina, renal insufficiency, premenstrual syndrome, cyclical oedema, Menières disease, hyperaldosteronism, pulmonary oedema, ascites, hypercalciuria, glaucoma, asthma, inflammation, pain, epilepsy, affective disorders, dementia and geriatric confusion, obesity, gastrointestinal disorders (including diarrhoea), hyperreninaemia, leukemia, and the modulation of gastric acid secretion.

The preparation of the compounds of the invention will now be more particularly illustrated by reference to the following experimental examples. The purity of compounds was routinely monitored by thin layer chromatography using Merck Kieselgel 60 $F_{254}$ plates. $^1$H-Nuclear magnetic resonance spectra were recorded using a Nicolet QE-300 spectrometer and were in all cases consistent with the proposed structures.

EXAMPLE 1

2-($N^2$-Acetyl-$N^6$-benzyloxycarbonyl-L-lysyl-aminomethyl)-3-{1-[(cis-4-ethoxycarbonyl-cyclohexyl)carbamoyl]cyclopentyl}propanoic acid t-butyl ester 1-Hydroxybenztriazole (207 mg, 1.53 mmole) and N-methylmorpholine (235 mg, 2.36 mmole) were added to a stirred solution of $N^2$-acetyl-$N^6$-benzyloxycarbonyl-L-lysine (456 mg, 1.41 mmole) in dry dichloromethane at 0° C., followed by 1-ethyl-3-(3-dimethylaminopropyl)carbodiimide (361 mg). The solution was stirred at 0° C. for 20 minutes and 3-{1-[(cis-4-ethoxycarbonyl-cyclohexyl)-carbamoyl]cyclopentyl}-2-(aminomethyl)-propanoic acid t-butyl ester (500 mg, 1.18 mmole) in dichloromethane (10 ml) was added in one portion and the reaction mixture allowed to warm to room temperature and stirred for 16 hours. The solution was concentrated under vacuum to a volume of 10 ml and partitioned between ethyl acetate and water. The organic phase was washed with water (2×50 ml), 2M hydrochloric acid (50 ml, 2×25 ml), sodium bicarbonate solution (2×25 ml) and brine and then dried (MgSO$_4$) and the solvent evaporated. The residue was chromatographed on silica eluting with ethyl acetate to give the title compound (610 g, 71%). Found: C,63.34; H,8.61; N,7.45. $C_{39}H_{60}N_4O_9$ (0.25H$_2$O) requires C,63.48; H,8.33; N,7.59%.

EXAMPLES 2-27

The following compounds were prepared by the general method of Example 1 using as starting materials either 3-{1-[(cis-4-ethoxycarbonyl-cyclohexyl)carbamoyl]cyclopentyl}-2-(aminomethyl)propanoic acid t-butyl ester(see Preparation 1) or the 3-ethoxycarbonyl isomer (see Preparation 2) and reacting with the appropriate acid of formula IV instead of $N^2$-acetyl-$N^6$-benzyloxycarbonyl-L-lysine.

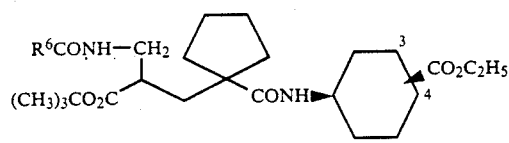

| Example | $R^6$ | $-CO_2C_2H_5$ attachment | Analysis % (Theoretical in brackets) | | |
|---|---|---|---|---|---|
| | | | C | H | N |
| 2 | # ZNH(CH$_2$)$_4$<br>    \|<br>C$_6$H$_5$CONHCH— | 4 | 66.59<br>(66.81 | 7.81<br>7.90 | 7.23<br>7.08) |
| 3 | C$_6$H$_5$CH$_2$<br>    \|<br>CH$_3$CONHCH— | 4 | 66.00<br>(66.53 | 8.38<br>8.38 | 6.86<br>6.85) |

-continued

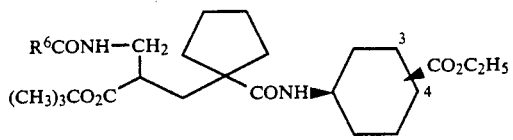

| Example | R⁶ | —CO₂C₂H₅ attachment | Analysis % (Theoretical in brackets) C | H | N |
|---|---|---|---|---|---|
| 4 | C₆H₅CH₂<br>\|<br>C₆H₅CONHCH— | 4 | 69.06<br>(69.31 | 8.16<br>7.90 | 6.18<br>6.22) |
| 5 | CH₃<br>\|<br>CH₃CONHCH— | 4 | 61.57<br>(62.54 | 8.64<br>8.81 | 7.69<br>7.82) |
| 6 | CH₃<br>\|<br>C₆H₅CONHCH— | 4 | 64.57<br>(66.08 | 8.21<br>8.24 | 6.68<br>7.01) |
| 7 | (CH₃)₂CH<br>\|<br>CH₃CONHCH— | 4 | 63.57<br>(63.69 | 9.11<br>9.09 | 7.26<br>7.43) |
| 8 | (CH₃)₂CH<br>\|<br>C₆H₅CONHCH— | 4 | 66.15<br>(66.96 | 8.67<br>8.51 | 6.85<br>6.69) |
| 9 | cyclopentyl-CH₃CONH | 3 | 64.69<br>(64.44 | 8.94<br>8.90 | 7.27<br>7.27) |
| 10 | cyclopentyl-C₆H₅CONH | 3 | 67.71<br>(67.58 | 8.24<br>8.35 | 6.34<br>6.57) |
| 11 | CH₃<br>\|<br>CH₃CONHC—<br>\|<br>CH₃ | 3 | 62.59<br>(63.13 | 8.80<br>8.95 | 7.63<br>7.62) |
| 12 | CH₃<br>\|<br>C₆H₅CONHC—<br>\|<br>CH₃ | 3 | 66.08<br>(66.53 | 8.49<br>8.38 | 6.75<br>6.85) |
| 13 | CH₃-C₆H₄-CONHCH(CH₃)— | 3 | 66.41<br>(66.53 | 8.35<br>8.38 | 6.63<br>6.85) |
| 14 | CH₃<br>\|<br>(CH₃)₂CHCONHCH— | 3 | 63.26<br>(63.69 | 9.28<br>9.09 | 7.16<br>7.43) |
| 15 | Cl-C₆H₄-CONHCH(CH₃)— | 3 | 61.98<br>(62.23 | 7.78<br>7.68 | 6.27<br>6.40)⁽¹⁾ |
| 16 | CH₃O-C₆H₄-CONHCH(CH₃)— | 3 | 64.67<br>(64.84 | 8.28<br>8.16 | 6.59<br>6.67) |

-continued

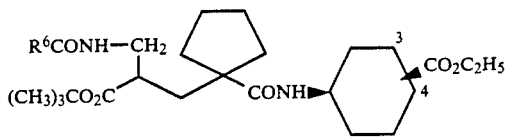

| Example | R⁶ | —CO₂C₂H₅ attachment | Analysis % (Theoretical in brackets) C | H | N |
|---|---|---|---|---|---|
| 17 | (naphthalen-2-yl)-CONHCH(CH₃)— | 3 | 67.94 (68.39 | 7.81 7.91 | 6.38 6.47) |
| 18 | ZNH(CH₂)₄ C₆H₅CH₂<br>C₆H₅CONH—CH—CONHCH— | 3 | 67.02 (67.21 | 7.57 7.66 | 7.20 7.40)[2] |
| 19 | ZNH(CH₂)₄ C₆H₅CH₂<br>CH₃CONH—CH CONHCH— | 3 | 66.02 (65.80 | 8.08 7.94 | 7.94 7.99) |
| 20 | ZNH(CH₂)₄ C₆H₃CH₂<br>cyclobutyl-CONH—CHCONH CH— | 3 | 65.70 (65.57 | 7.98 8.09 | 7.46 7.50)[3] |
| 21 | ZNH(CH₂)₄<br>cyclobutyl-CONH—CH— | 3 | 64.47 (65.60 | 8.21 8.39 | 7.22 7.29) |
| 22 | (naphthalen-2-yl)-CONH—CH(ZNH(CH₂)₄)— | 3 | 68.27 (68.55 | 7.77 7.67 | 6.56 6.66) |
| 23 | (CH₃)₃COCONH-[pyrrolidine with N-COC₆H₅ and S] | 3 | 63.84 (64.00 | 8.13 8.20 | 7.37 7.45)[2] |
| 24 | ZNH(CH₂)₄<br>CH₃SO₂NH—CH— | 3 | 58.65 (59.66 | 7.84 7.91 | 7.17 7.32) |
| 25 | ZNH<br>ZNH(CH₂)₄—CH— | 3 | 63.29 (63.29 | 7.73 7.59 | 6.49 6.49)[4] |
| 26 | ZNH(CH₂)₄<br>CH₃CONH—CH— | 3 | 63.65 (64.26 | 8.39 8.30 | 7.63 7.69) |
| 27 | ZNH(CH₂)₄<br>C₆H₅CONH—CH— | 3 | 66.95 (66.81 | 7.95 7.90 | 6.75 7.08) |

Z = C₆H₅CH₂OCO—
[1] 0.25 mole CH₃CO₂C₂H₅
[2] 0.5 H₂O
[3] 1.0 H₂O
[4] 0.5 mole CH₂Cl₂

EXAMPLES 28–29

The following compounds were prepared following the general method of Example 1 using as starting material 3-{1-[(cis-3-ethoxycarbonyl-cyclohexyl)carbamoyl]cyclopentyl}-2-aminopropanoic acid and reacting with the appropriate acid of formula IV.

| Example | R⁶ | Analysis % (Theoretical in brackets) | | |
|---|---|---|---|---|
| | | C | H | N |
| 28 | [3-pyridyl]-CONH-CH(ZNH(CH₂)₄)- | 64.17 (64.10 | 7.71 7.69 | 8.79 8.90)[1] |
| 29 | C₆H₅CH₂CO-[phenyl]-CONH-CH(ZNH(CH₂)₄)- | 67.73 (68.00 | 7.62 7.53 | 6.16 6.34) |

[1] hemihydrate

EXAMPLES 30–33

The following compounds were prepared following the general method of Example 1 using the appropriate amine of formula (III) and coupling with $N^2$-acetyl-$N^6$-benzyloxycarbonyl-L-lysine.

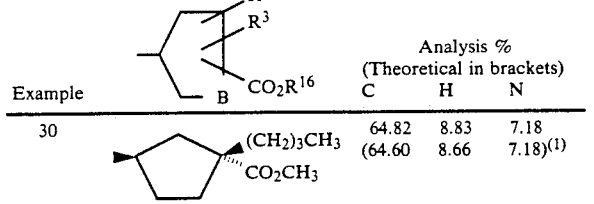

| Example | —B—[structure]—CO₂R¹⁶ | Analysis % (Theoretical in brackets) | | |
|---|---|---|---|---|
| | | C | H | N |
| 30 | cyclopentyl (CH₂)₃CH₃, CO₂CH₃ R,S | 64.82 (64.60 | 8.83 8.66 | 7.18 7.18)[1] |
| 31 | cyclohexyl CO₂C₂H₅, (CH₂)₃CH₃ | 63.69 (63.59 | 8.43 8.81 | 6.94 6.90)[2] |
| 32 | cyclohexyl (CH₂)₃CH₃, CO₂C₂H₅ diastereoisomers | 65.95 (65.79 64.52 (64.31 | 8.90 8.73 8.33 8.78 | 6.83 7.14 6.43 6.97)[3] |

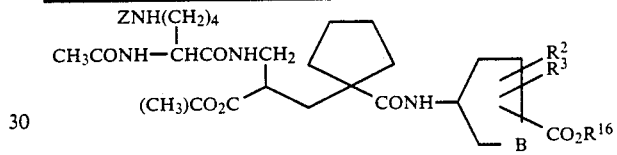

| Example | —B—[structure]—CO₂R¹⁶ | Analysis % (Theoretical in brackets) | | |
|---|---|---|---|---|
| | | C | H | N |
| 33 | cyclohexyl (CH₂)₃CH₃, CO₂C₂H₅ | 65.94 (65.79 | 8.83 8.73 | 7.14 7.14) |

[1] Hemihydrate
[2] 1.5 hydrate
[3] hydrate

EXAMPLE 34

N-[4-{1-[cis-3-t-butoxycarbonylcyclohexyl)-carbamoyl]cyclopentyl}-3-(t-butoxycarbonyl)-butanoyl]-phenylalanine t-butyl ester.

1-Hydroxybenztriazole (76 mg, 0.576 mmol) and N-methylmorpholine (0.5 ml, 4.5 mmole) were added to a stirred solution of 3-{1-[(cis-3-t-butoxycarbonylcyclohexyl)-carbamoyl]cyclopentyl}-2-(carboxymethyl)-propanoic acid t-butyl ester (219.6 mg, 0.457 mmol) in dry dichloromethane (20 ml) at 0° C. followed by 1-ethyl-3-(dimethylaminopropyl)carbodimide (94 mg). The solution was stirred at 0° C. for 20 minutes and phenylalanine t-butyl ester (128 mg, 0.5 mmol) in dry dichloromethane (5 ml) added in one portion, and the reaction allowed to warm up to room temperature and stirred for 16 hours. The solution was concentrated under vacuum to a volume of 10 ml, and partitioned between ethyl acetate and water. The organic phase was washed with water (2×25 ml), 2M hydrochloric acid (2×10 ml), sodium bicarbonate solution (2×10 ml) and brine, and dried (MgSO₄) and the solvent evaporated to yield the title compound as an oil (325 mg, 100%).
Found: C,66.59; H,8.92; N,4.25. $C_{39}H_{60}N_2O_8 \cdot H_2O$ requires C,66.63; H,8.89; N,3.49%.

EXAMPLES 35–38

The following compounds were prepared following the procedure of example 34 using as starting material the appropriate 3-{1-[cis-3-alkoxycarbonyl-cyclohexyl)carbamoyl]cyclopentyl}-2-carboxy-methyl-propanoic acid t-butyl ester and reacting with the appropriate amine of formula $R^7R^9NH$.

(2 ml) and dichloromethane (1 ml). The solution was kept at 4° C. overnight, then concentrated to dryness under vacuum, and the residue was azeotroped six times with dichloromethane. The resulting crude product was then taken up in ethyl acetate and washed with water until the washings were neutral. The organic phase was dried (MgSO4) and evaporated under vacuum to afford the title compound (442 mg, 84%) as a white foam.
Found: C,61.89; H,7.76; N,7.93. $C_{35}H_{52}N_4O_9$ (0.5 $H_2O$) requires C,61.65; H,7.69; N,8.22%.

EXAMPLES 40 to 65

| Example | $R^7$ | $R^{16}$ | Analysis % (Theoretical in brackets) | | |
|---|---|---|---|---|---|
| | | | C | H | N |
| 35 | (CH3)2NCO<br>\|<br>ZNH(CH2)4CH— | —C(CH3)3 | 63.39<br>(63.39 | 8.38<br>8.38 | 6.95<br>6.98)[1] |
| 36 | (CH3)2CHNHCO<br>\|<br>ZNH(CH2)4—CH— | —C2H5 | 63.83<br>(63.96 | 8.40<br>8.59 | 7.01<br>6.63) |
| 37 | ⟨pyrrolidinyl⟩NCO<br>\|<br>ZNH(CH2)4—CH— | —C2H5 | 65.17<br>(65.60 | 8.39<br>8.39 | 7.10<br>7.29) |
| 38 | 3-pyridyl-CONH—<br>\|<br>ZNH(CH2)4—CH— | —C2H5 | 63.17<br>(63.11 | 7.73<br>7.54 | 8.28<br>8.48) |

[1] 0.4 mole $CH_2Cl_2$

EXAMPLE 39

2-(N²-Acetyl-N⁶-benzyloxycarbonyl-L-lysyl-aminomethyl)-3-{1-[(cis-4-ethoxycarbonylcyclohexyl)carbamoyl]cyclopentyl}propanoic acid

The t-butyl ester from Example 1 (571 mg, 0.783 mmol) was dissolved in a mixture of trifluoroacetic acid The following compounds were prepared following the procedure of Example 39 but using as starting material the appropriate t-butyl ester of Examples 2 to 27.

| Example | $R^6$ | —CO2C2H5 attachment | Analysis % (Theoretical in brackets) | | |
|---|---|---|---|---|---|
| | | | C | H | N |
| 40 | ZNH(CH2)4<br>\|<br>C6H5CONHCH— | 4 | 65.02<br>(65.37 | 7.33<br>7.41 | 7.60<br>7.61) |
| 41 | C6H5CH2<br>\|<br>CH3CONHCH— | 4 | 64.18<br>(64.61 | 7.54<br>7.77 | 7.63<br>7.54) |
| 42 | C6H5CH2<br>\|<br>C6H5CONHCH— | 4 | 66.94<br>(67.83 | 7.34<br>7.32 | 6.65<br>6.78) |

-continued
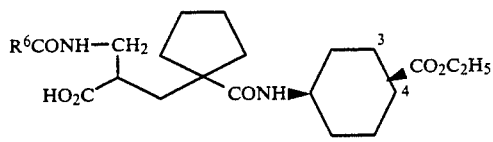
| Example | R⁶ | —CO₂C₂H₅ attachment | Analysis % (Theoretical in brackets) | | |
|---|---|---|---|---|---|
| | | | C | H | N |
| 43 | CH₃CONHCH(CH₃)— | 4 | 49.96 (49.69 | 6.49 6.26 | 6.50 6.44)[1] |
| 44 | C₆H₅CONHCH(CH₃)— | 4 | 63.67 (64.07 | 7.80 7.60 | 7.52 7.73) |
| 45 | CH₃CONHCH[CH(CH₃)₂]— | 4 | 60.89 (61.27 | 8.58 8.50 | 8.14 8.25) |
| 46 | C₆H₅CONHCH[CH(CH₃)₂]— | 4 | 64.88 (65.12 | 7.95 7.93 | 7.34 7.35) |
| 47 | CH₃CONH-cyclopentyl | 3 | 62.11 (62.16 | 8.44 8.31 | 7.95 8.06) |
| 48 | C₆H₅CONH-cyclopentyl | 3 | 65.49 (65.85 | 7.80 7.77 | 6.99 7.20) |
| 49 | CH₃CONH—C(CH₃)₂— | 3 | 60.20 (60.58 | 8.46 8.34 | 8.30 8.48) |
| 50 | C₆H₅CONH—C(CH₃)₂— | 3 | 64.86 (64.61 | 7.91 7.77 | 7.24 7.54) |
| 51 | 4-CH₃-C₆H₄-CONHCH(CH₃)— | 3 | 64.61 (64.61 | 7.96 7.77 | 7.33 7.54) |
| 52 | (CH₃)₂CHCONHCH(CH₃)— | 3 | 61.08 (61.27 | 8.52 8.50 | 7.91 8.25) |
| 53 | 4-Cl-C₆H₄-CONHCH(CH₃)— | 3 | 60.24 (60.25 | 7.19 6.97 | 6.90 7.27) |
| 54 | 4-CH₃O-C₆H₄-CONHCH(CH₃)— | 3 | 62.19 (62.32 | 7.59 7.58 | 7.15 7.27)[2] |
| 55 | 2-naphthyl-CONHCH(CH₃)— | 3 | 66.10 (66.09 | 7.21 7.33 | 6.97 7.01)[3] |

-continued

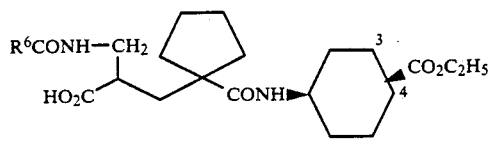

| Example | R⁶ | —CO₂C₂H₅ attachment | Analysis % (Theoretical in brackets) C | H | N |
|---|---|---|---|---|---|
| 56 | ZNH(CH₂)₄    C₆H₅CH₂<br>\|               \|<br>C₆H₅CONHCH—CONH—CH— | 3 | 63.70<br>(63.65 | 6.87<br>6.98 | 7.53<br>7.56)[4] |
| 57 | ZNH(CH₂)₄    C₆H₅CH₂<br>\|               \|<br>CH₃CONHCH—CONH—CH— | 3 | 63.83<br>(63.75 | 7.59<br>7.54 | 8.32<br>8.45)[5] |
| 58 | ZNH(CH₂)₄    C₆H₅CH₂<br>\|               \|<br>▱—CONHCH—CONH—CH | 3 | 65.41<br>(65.63 | 7.66<br>7.62 | 8.01<br>8.14) |
| 59 | ZNH—(CH₂)₄<br>\|<br>▱—CONH—CH— | 3 | 62.16<br>(64.02 | 7.95<br>7.92 | 7.62<br>7.80) |
| 60 | naphthyl—CONH—CH(—(CH₂)₄—NH₂)— | 3[8] | gum Rf 0.33 (silica) | | |
| 61 | pyrrolidine with N—COC₆H₅, H₂N, S substituents | 3 | 58.34<br>(58.25 | 7.38<br>7.41 | 8.60<br>8.77)[6] |
| 62 | ZNH(CH₂)₄<br>\|<br>CH₃SO₂NH—CH— | 3 | 57.40<br>(57.61 | 7.48<br>7.40 | 7.89<br>7.90) |
| 63 | ZNH<br>\|<br>ZNH(CH₂)₄—CH | 3 | 63.20<br>(63.02 | 7.47<br>7.25 | 7.23<br>7.13) |
| 64 | ZNH(CH₂)₄<br>\|<br>CH₃CONH—CH— | 3 | 60.54<br>(60.79 | 7.81<br>7.63 | 7.94<br>8.07) |
| 65 | ZNH(CH₂)₄<br>\|<br>C₆H₅CONH—CH— | 3 | 64.53<br>(64.79 | 7.29<br>7.35 | 7.36<br>7.54)[9] |

[1] 1.5 mole CF₃CO₂H
[2] 0.25 mole H₂O
[3] 0.33 mole H₂O
[4] 0.5 mole CH₂Cl₂
[5] 0.5 mole H₂O
[6] HCl in CH₂Cl₂ at 0° C. for 3 hours used instead of trifluoroacetic acid. Product isolated as .HCl.H₂O.
[7] 0.1 mole CH₂Cl₂.
[8] From Example 106.

EXAMPLES 66-67

The following compounds were prepared following the general method of Example 39 using as starting material the appropriate t-butyl ester of Examples 28 and 29.

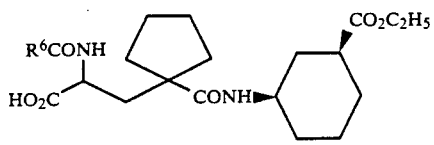

| Example | R⁶ | Analysis % (Theoretical in brackets) | | |
|---|---|---|---|---|
| | | C | H | N |
| 66 | [pyridyl-CONH-CH(ZNH(CH₂)₄)-] | 61.79 (62.07 | 7.19 7.20 | 9.39 9.52)⁽¹⁾ |
| 67 | C₆H₅CH₂CO-[phenyl]-CONH-CH(ZNH(CH₂)₄)- | foam | | |

⁽¹⁾0.75 H₂O

EXAMPLES 68-71

The following compounds were prepared by the general method of Example 39 using the appropriate t-butyl ester of Examples 30 to 33.

| Example | B (substituent) | Analysis % (Theoretical in Brackets) | | |
|---|---|---|---|---|
| | | C | H | N |
| 68 | (CH₂)₃CH₃, CO₂CH₃ (cyclopentyl) | 60.74 (61.05 | 7.97 7.85 | 7.42 7.40)⁽¹⁾ |
| 69 | CO₂C₂H₅, (CH₂)₃CH₃ (cyclohexyl) | 62.64 (62.71 | 8.22 8.37 | 7.47 7.50) |
| 70 | (CH₂)₃CH₃, CO₂C₂H₅ (cyclohexyl) | two diastereoisomers isolated as gums | | |
| 71 | (CH₂)₃CH₃, CO₂C₂H₅ (cyclohexyl) | gum | | |

EXAMPLES 72-76

The following compounds were prepared by the general method of Example 39 using the appropriate t-butyl ester of Examples 34-38.

| Example | R⁷ | R⁴ | Analysis % (Theoretical in brackets) | | |
|---|---|---|---|---|---|
| | | | C | H | N |
| 72 | C₆H₅CH₂—CH(CO₂H)— | H | 61.49 (62.13 | 7.29 7.19 | 4.64 4.28)⁽¹⁾ |
| 73 | (CH₃)₂NCO—CH(ZNH(CH₂)₄)— | H | 60.98 (60.95 | 7.47 7.71 | 7.86 8.36)⁽²⁾ |
| 74 | (CH₃)₂CHNHCO—CH(ZNH(CH₂)₄)— | C₂H₅ | 59.78 (59.79 | 7.65 7.53 | 7.14 7.40) |
| 75 | pyrrolidinyl-N—CO—CH(ZNH(CH₂)₄)— | C₂H₅ | 60.58 (60.70 | 7.55 7.55 | 7.23 7.33) |
| 76 | pyridyl-NHCO—CH(ZNH(CH₂)₄)— | C₂H₅ | 62.01 (61.81 | 7.01 7.08 | 8.86 9.16) |

⁽¹⁾0.5 mole CH₃CO₂C₂H₅
⁽²⁾0.6 H₂O

EXAMPLE 77

2-(N²-Acetyl-N⁶-benzyloxycarbonyl-L-lysyl-aminomethyl)-3-{1-[(cis-4-carboxycyclohexyl)carbamoyl]cyclopentyl}propanoic acid The ethyl ester from Example 39 (404 mg, 0.600 mmol) was dissolved in 2M sodium hydroxide solution (10 ml), and the resulting solution was kept at room temperature overnight. The reaction mixture was diluted to 30 ml and extracted with diethyl ether. The aqueous phase was acidified to pH 1 with 2M hydrochloric acid and extracted with ethyl acetate (3×25 ml). The organic phase was dried (MgSO$_4$) and evaporated to afford the title compound (375 mg, 97%) as a white foam. Found: C,58.30; H,7.24; N,8.20. C$_{33}$H$_{48}$N$_4$O$_9$. (0.25 CH$_2$Cl$_2$, 1.25 H$_2$O) requires C,58.00; H,7.17; N,8.14%.

EXAMPLES 78–96

The following compounds were prepared following the procedure of Example 77 but using as starting material the appropriate ethyl ester of Examples 40 to 58.

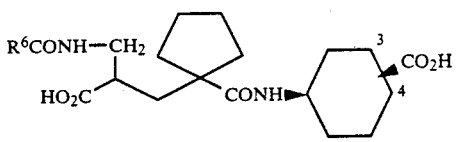

| Example | R⁶ | —CO$_2$H attachment | C | H | N |
|---|---|---|---|---|---|
| 78 | ZNH(CH$_2$)$_4$<br>\|<br>C$_6$H$_5$CONHCH— | 4 | 63.42<br>(63.94 | 7.16<br>7.34 | 7.48<br>7.68)⁽¹⁾ |
| 79 | C$_6$H$_5$CH$_2$<br>\|<br>CH$_3$CONHCH— | 4 | 61.34<br>(61.50 | 7.47<br>7.39 | 7.57<br>7.65)⁽²⁾ |
| 80 | C$_6$H$_5$CH$_2$<br>\|<br>C$_6$H$_5$CONHCH— | 4 | 65.39<br>(65.49 | 6.84<br>7.08 | 6.92<br>6.94)⁽³⁾ |
| 81 | CH$_3$<br>\|<br>CH$_3$CONHCH— | 4 | 52.87<br>(52.67 | 6.66<br>6.97 | 8.34<br>8.01)⁽⁴⁾ |
| 82 | CH$_3$<br>\|<br>C$_6$H$_5$CONHCH— | 4 | 60.78<br>(60.82 | 7.19<br>7.11 | 7.73<br>7.82)⁽⁵⁾ |
| 83 | (CH$_3$)$_2$CH<br>\|<br>CH$_3$CONHCH— | 4 | 58.16<br>(58.16 | 8.03<br>8.08 | 8.18<br>8.43)⁽⁶⁾ |
| 84 | (CH$_3$)$_2$CH<br>\|<br>C$_6$H$_5$CONHCH— | 4 | 63.30<br>(63.49 | 7.75<br>7.70 | 7.17<br>7.25)⁽⁷⁾ |
| 85 | CH$_3$CONH-cyclopentyl | 3 | 59.52<br>(59.74 | 8.04<br>8.02 | 8.07<br>8.36)⁽¹⁾ |
| 86 | C$_6$H$_5$CONH-cyclopentyl | 3 | 64.68<br>(64.84 | 7.62<br>7.44 | 7.15<br>7.56) |
| 87 | CH$_3$<br>\|<br>CH$_3$CONH—C—<br>\|<br>CH$_3$ | 3 | 55.66<br>(56.09 | 7.71<br>7.80 | 8.31<br>8.44)⁽⁸⁾ |
| 88 | CH$_3$—<br>\|<br>C$_6$H$_5$CONHC—<br>\|<br>CH$_3$ | 3 | 62.77<br>(63.13 | 7.57<br>7.63 | 7.31<br>7.44)⁽⁹⁾ |
| 89 | CH$_3$-C$_6$H$_4$-CONHCH(CH$_3$)— | 3 | 62.38<br>(62.43 | 7.47<br>7.49 | 7.60<br>7.80)⁽¹⁾ |

-continued

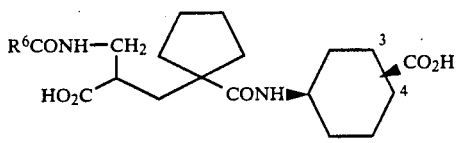

| Example | R⁶ | —CO₂H attachment | Analysis % (Theoretical in brackets) C | H | N |
|---|---|---|---|---|---|
| 90 | (CH₃)₂CHCONHCH(CH₃)— | 3 | 58.73 (58.75 | 8.21 8.22 | 8.32 8.57)[1] |
| 91 | 4-Cl-C₆H₄-CONHCH(CH₃)— | 3 | 57.76 (58.00 | 6.66 6.67 | 7.30 7.52)[1] |
| 92 | 4-CH₃O-C₆H₄-CONHCH(CH₃)— | 3 | 60.81 (60.63 | 7.25 7.27 | 7.57 7.58)[1] |
| 93 | 2-naphthyl-CONHCH(CH₃)— | 3 | 64.52 (64.48 | 7.15 7.08 | 6.98 7.09)[10] |
| 94 | C₆H₅CONH—CH(ZNH(CH₂)₄)—CONH—CH(C₆H₅CH₂)— | 3 | 65.12 (65.41 | 7.07 7.01 | 7.88 8.12)[1] |
| 95 | CH₃CONH—CH(ZNH(CH₂)₄)—CONH—CH(C₆H₅CH₂)— | 3 | 63.19 (62.98 | 7.27 7.30 | 8.11 8.74)[1] |
| 96 | cyclopropyl-CONH—CH(ZNH(CH₂)₄)—CONH—CH(C₆H₅CH₂)— | 3 | 64.24 (64.26 | 7.42 7.43 | 8.11 8.33)[1] |

[1] 0.5 mole H₂O;
[2] 0.125 mole CH₂Cl₂; 0.5 mole H₂O;
[3] 0.75 mole H₂O;
[4] 0.5 mole CH₂Cl₂; 0.25 mole CF₃CO₂H;
[5] 0.2 mole CH₂Cl₂; 0.25 mole H₂O;
[6] 0.125 mole CH₂Cl₂; 0.33 mole H₂O;
[7] 0.4 mole CH₃CO₂C₂H₅;
[8] 0.25 mole CH₂Cl₂; 0.5 mole H₂O;
[9] 0.28 mole CH₃CO₂C₂H₅; 0.14 mole H₂O;
[10] 0.2 mole CH₃CO₂C₂H₅; 0.5 mole H₂O.

EXAMPLE 97

2-(N²-Acetyl-L-lysyl-aminomethyl)-3-{1-[(cis-4-carboxycyclohexyl)carbamoyl]cyclopentyl}propanoic acid A solution of the product from Example 77 (200 mg, 0.31 mmol) in a mixture of ethanol (27 ml) and water (3 ml) was reduced on 10% palladium on charcoal (20 mg) under 50 p.s.i. (3.46 bar) of hydrogen for 1½ hours. The solution was filtered and the solvent evaporated under vacuum, and the residue azeotroped with dichloromethane (6x) to afford the title compound (161 mg, 100%) as a white solid, m.p. 161°–163° C. Found: C,56.80; H,8.49; N,9.22. $C_{25}H_{42}N_4O_7 \cdot H_2O$ requires C,56.80; H,8.39; N,10.60%.

EXAMPLES 98–110

The following compounds were prepared following the procedure of Example 97 but using as starting material the appropriate amino-protected ethyl ester or acid.

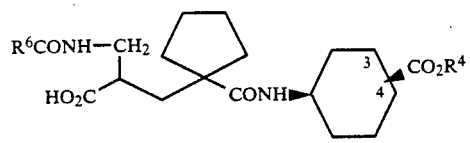

| Example | R⁶ | —CO₂R⁴ attachment | Analysis % (Theoretical in brackets) C | H | N |
|---|---|---|---|---|---|
| 99 | C₆H₅CONHCH(H₂N(CH₂)₄)—CONH—CH(C₆H₅CH₂)— | 3-CO₂C₂H₅ | 64.48 (64.29 | 7.96 7.76 | 8.21 9.14)[1] |
| 100 | C₆H₅CONHCH(H₂N(CH₂)₄)—CONH—CH(C₆H₅CH₂)— | 3-CO₂H | 63.57 (63.48 | 7.68 7.51 | 8.46 9.49)[1] |
| 101 | CH₃CONHCH(H₂N(CH₂)₄)—CONH—CH(C₆H₃CH₂)— | 3-CO₂C₂H₅ | 61.74 (61.43 | 8.27 8.16 | 9.20 9.95)[1] |
| 102 | CH₃CONHCH(H₂N(CH₂)₄)—CONH—CH(C₆H₅CH₂)— | 3-CO₂H | 60.54 (60.42 | 7.93 7.91 | 9.97 10.36)[1] |
| 103 | ▭—CONHCH(H₂N(CH₂)₄)—CONH—CH(C₆H₅CH₂)— | 3-CO₂C₂H₅ | 64.03 (64.13 | 8.41 8.21 | 8.48 9.59)[2] |
| 104 | ▭—CONH—CH(H₂N(CH₂)₄)—CONH—CH(C₆H₅CH₂)— | 3-CO₂H | 62.16 (62.08 | 8.08 8.03 | 9.58 9.78)[1] |
| 105 | ▭—CONH—CH(H₂N(CH₂)₄)— | 3-CO₂C₂H₅ | 58.87 (60.88 | 8.50 8.53 | 8.88 9.41)[3] |
| 106 | (naphthyl)—CONH—CH(H₂N(CH₂)₄)— (6) | 3-CO₂C₂H₅ | gum | | |
| 107 | CH₃SO₂NH—CH(H₂N(CH₂)₄)— | 3-CO₂C₂H₅ | 51.75 (52.50 | 8.07 7.89 | 8.83 9.33)[4] |
| 108 | H₂N(CH₂)₄—CH(NH₂)— | 3-CO₂C₂H₅ | 57.07 (59.15 | 8.85 8.84 | 10.12 10.99)[5] |
| 109 | CH₃CONH—CH(H₂N(CH₂)₄)— | 3-CO₂C₂H₅ | 55.63 (57.32 | 8.42 8.73 | 9.27 9.91)[6] |
| 110 | C₆H₅CONH—CH(H₂N(CH₂)₄)— | 3-CO₂C₂H₅ | 62.46 (62.12 | 8.17 8.15 | 8.65 9.06)[1] |

[1] Hydrate
[2] 0.25 H₂O
[3] 0.2 mole CH₂Cl₂
[4] 0.25 mole H₂O, 0.25 mole CH₂Cl₂
[5] 0.25 mole H₂O, 0.1 CH₂Cl₂
[6] From Example 22, t-butyl ester.

EXAMPLES 111–112

The following compounds were prepared from Examples 66 and 67 by the hydrolysis of the ester group following the general procedure of Example 77 followed by catalytic hydrogenation or by treatment with HBr in glacial acetic acid to remove the benzyloxycarbonyl protecting group.

| | | C | H | N |
|---|---|---|---|---|
| 111 | [pyridin-3-yl-CONH-CH(H₂N(CH₂)₄)-] | 59.24 (59.14 | 7.62 7.44 | 12.15 12.32)[1] |
| 112 | [4-HO-C₆H₄-CONH-CH(H₂N(CH₂)₄)-] | foam | | |

[1] 0.5 mole H₂O

EXAMPLES 113–119

The following Examples were prepared from Examples 73 to 76 by catalytic hydrogenation according to the procedure of Example 97, followed, in the case of the ethyl esters, by hydrolysis according to the procedure of Example 77. The diacids were isolated by ion-exchange chromatography eluting with aqueous pyridine.

[Structure: R⁷NHCO-CH₂-C(cyclopentane)-CH(HO₂C-CH₂-)-... CONH-cyclohexyl-CO₂R⁴]

| Example | R⁷ | R⁴ | C | H | N |
|---|---|---|---|---|---|
| 113 | (CH₃)₂NCO–NH–CH(H₂N(CH₂)₄)– | H | 55.62 (55.62 | 8.37 9.57 | 7.95 7.95)[1] |

-continued

[Structure: R⁷NHCO-CH₂-C(cyclopentane)-CH(HO₂C-)... CONH-cyclohexyl-CO₂R⁴]

| Example | R⁷ | R⁴ | C | H | N |
|---|---|---|---|---|---|
| 114 | (CH₃)₂CHNHCO–CH(H₂N(CH₂)₄)– | C₂H₅ | 60.10 (59.82 | 8.71 8.79 | 8.34 8.67 |
| 115 | | H | 56.27 (56.42 | 8.37 8.77 | 9.79 9.74) |
| 116 | pyrrolidin-N-CO–CH(H₂N(CH₂)₄)– | C₂H₅ | 59.52 (59.35 | 8.51 8.76 | 8.53 8.92) |
| 117 | | H | 59.14 (58.97 | 8.46 8.53 | 9.35 9.48) |
| 118 | pyridin-3-yl-NHCO–CH(H₂N(CH₂)₄)– | C₂H₅ | 59.02 (58.88 | 7.81 7.75 | 10.55 10.33) |
| 119 | | H | 56.79 (60.72 | 8.01 7.55 | 9.08 12.21) |

[1] 3.3 moles C₂H₅OH, 1.5 mole H₂O

EXAMPLES 120–125

The following compounds were prepared by hydrolysis of the appropriate ester of Examples 61 or 105–110 following the procedure of Example 77. The products were isolated by ion-exchange chromatography eluting with aqueous pyridine.

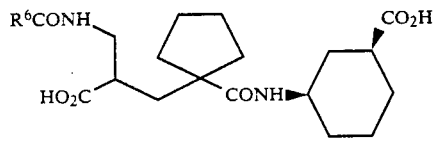

[Structure: R⁶CONH-CH₂-C(cyclopentane)-CH(HO₂C-)... CONH-cyclohexyl-CO₂H]

| Example | R⁶ | C | H | N |
|---|---|---|---|---|
| 120 | cyclobutyl-CONH-CH(H₂N(CH₂)₄)– | 57.36 (59.13 | 8.29 8.51 | 9.28 9.85)[1] |
| 121 | naphthalen-2-yl-CONH-CH(H₂N(CH₂)₄)– | 64.43 (64.64 | 7.60 7.50 | 8.95 8.87)[2] |
| 122 | (1-COC₆H₅-4-H₂N-pyrrolidin-2-yl,S)– | 61.54 (61.58 | 7.59 7.30 | 9.90 9.90)[2] |
| 123 | CH₃SO₂NH–CH(H₂N(CH₂)₄)– | 50.32 (52.38 | 7.86 7.77 | 9.04 10.18)[3] |
| 124 | NH₂–CH(H₂N(CH₂)₄)– | 53.61 (57.30 | 8.55 8.68 | 10.69 11.62)[4] |

|         |                              | Analysis % (Theoretical in brackets) |      |           |
|---------|------------------------------|-------|-------|-----------|
| Example | $R^6$                        | C     | H     | N         |
| 125     | $H_2N(CH_2)_4$<br>\|<br>$CH_3CONH-CH-$ | 56.57<br>(56.79 | 8.55<br>8.39 | 10.19<br>10.60)[1] |
| 126     | $H_2N(CH_2)_4$<br>\|<br>$C_6H_5CONH-CH-$ | 60.85<br>(60.67 | 7.96<br>8.05 | 8.69<br>9.13)[5] |

[1] hydrate
[2] 0.5 mole $H_2O$
[3] 0.2 mole $H_2O$
[4] 0.75 mole $H_2O$
[5] 1.0 mole $H_2O$ 0.5 mole $C_2H_5OH$

EXAMPLES 127–134

The following compounds were prepared from Examples 68–71 by catalytic hydrogenation according to the procedure of Example 97 to yield the esters ($R^4=CH_3$ or $C_2H_5$) followed by hydrolysis following the procedure of Example 77 to yield the corresponding acids ($R^4=H$).

| Example | B | $R^4$ | Analysis % (Theoretical in brackets) | | |
|---------|---|-------|-------|-------|-------|
|         |   |       | C     | H     | N     |
| 127     | cyclopentane with $(CH_2)_3CH_3$ and $CO_2R^4$ | $CH_3$ | 59.19<br>(58.85 | 8.93<br>9.13 | 8.62<br>9.15)[1] |
| 128     |   | H | 60.12<br>(60.01 | 9.00<br>8.94 | 9.88<br>9.65)[2] |
| 129     | cyclohexane with $CO_2R^4$ and $(CH_2)_3CH_3$ | $C_2H_5$ | 60.05<br>(60.13 | 8.97<br>8.81 | 8.55<br>8.93)[3] |
| 130     |   | H | 58.59<br>(58.54 | 8.97<br>9.08 | 8.85<br>9.26)[4] |

[1] 1.75 $H_2O$
[2] 0.75 $H_2O$
[3] 0.4 mole $CH_2Cl_2$
[4] 1.5 $H_2O$, 0.25 $C_2H_5OH$

| 131 | cyclohexane with $(CH_2)_3CH_3$ and $CO_2R^4$ | $C_2H_5$ | products obtained as gums | | |
| 132 |   | H | (I) 60.40<br>(II) 60.64<br>(60.50 | 8.80<br>8.87<br>8.93 | 9.65[1]<br>9.80[1]<br>9.73) |
|     |   |   | (two diastereoisomers) | | |
| 133 | cyclohexane with $(CH_2)_3CH_3$ and $CO_2R^4$ | $C_2H_5$ | gum | | |
| 134 |   | H | 60.29<br>(60.50 | 9.11<br>8.93 | 9.68<br>9.73)[1] |

[1] 0.5 $H_2O$

EXAMPLE 135

2-(N²-Methanesulphonyl-L-lysyl-aminomethyl)-3-{1-[(cis-4-carboxycis-3-butylcyclohexyl)carbamoyl]cyclopentyl}propanoic acid

1. 3-(1-Carboxycyclopentyl)-2-aminopropanoic acid t-butyl ester 3-(1-Carboxycyclopentyl)-2-(dibenzylaminomethyl)-propanoic acid t-butyl ester hydrochloride (20.0 g; 41 mmol) in ethanol (160 ml) and triethylamine (2.0 ml) was hydrogenated over palladium (from 20% Pd(OH)$_2$/C; 20 g) at 60 p.s.i. (4.1 bar). After eighteen hours the mixture was filtered through arbicel, the solvent evaporated and the residue dried azeotropically with toluene. The required primary amino acid triethylamine salt, containing one mole equivalent of triethylamine hydrochloride was thus obtained as a white solid (16.21 g).

2. 2-(N²-Benzyloxycarbonyl-N⁶-t-butoxycarbonyl-L-lysylaminomethyl)-3-[1-(1-carboxycyclopentyl)]-propanoic acid t-butyl ester (diastereoisomer)

The above product (8.24 g; 20.1 mmole) and N²-benzyloxycarbonyl-N⁶-t-butoxycarbonyl-L-lysine 4-nitrophenyl ester (9.50 g, 18.9 mmole) were dissolved in dry methylene chloride (70 ml). The solution was stirred and after cooling to 10° C., triethylamine (2.64 ml, 18.9 mmol) was added. After half an hour the mixture became homogenous and was allowed to stand at room temperature overnight. The solution was then washed with 1M citric acid followed by water, dried over MgSO$_4$ and evaporated. The residue was purified by chromatography on silica gel (500 g) eluting with increasing proportions of ethyl acetate in hexane (2:1 to 4:1) and finally with ethylacetate, hexane, acetic acid (4:1:0.05). The required mixture of diastereoisomers were then separated by chromatography on silica gel (1 kg) eluting with a mixture of toluene, isopropanol and diethylamine (10:2:1). The diethylamine salt of the required more polar diastereoisomer was obtained as an orange foam (3.01 g), which was dissolved in ethyl acetate and washed with 1M citric acid and brine. Drying over MgSO$_4$ and evaporation gave the free acid as a yellow foam (2.81 g). Found: C,62.89; H,8.29; N,6.69. C$_{33}$H$_{51}$N$_3$O$_9$ requires C,62.54; H,8.11; N,6.63%. Additional chromatography of a small sample on silica eluting with increasing proportions of ethyl acetate in hexane (2:3 to 17:3) gave a cream powder $[\alpha]_D^{25} -2.8°$, $[\alpha]_{365}^{25} -3.6°$ (c=0.5, ethanol).

3. 2-(N²-Benzyloxycarbonyl-N⁶-t-butoxycarbonyl-L-lysylaminomethyl)-3-{1-[(cis-4-ethoxycarbonyl-cis-3-butylcyclohexyl)-carbamoyl]cyclopentyl}propanoic acid t-butyl ester Coupling of the above product from step 2 (650 mg; 1.03 mmole) with c-4-amino-c-2-butyl-r-1-cyclohexane carboxylic acid ethyl ester hydrochloride (271 mg; 1.03 mmole) as described in Example 1 followed by chromatography on silica eluting with increasing proportions of ethyl acetate in hexane (7:3 to 4:6) gave the required product as a pale foam (630 mg; 73%).

Found: C,64.37; H,8.98; N,6.81. C$_{46}$H$_{74}$N$_4$O$_{10}$ (0.75 H$_2$O) requires C,64.50; H,8.88; N,6.54%.

4. 2-(N²-Methanesulphonyl-L-lysyl-aminomethyl)-3-{1-[(cis-4-carboxy-cis-3-butylcyclohexyl)carbamoyl]cyclopentyl}propanoic acid i) The above product from step 3 (620 mg; 0.735 mmole) in ethanol (18 ml) and water (2 ml) was hydrogenated over 5% palladium on carbon (200 mg) at 50 p.s.i. (3.5 bar). After three hours the mixture was filtered through Arbicel and evaporated to dryness giving a white foam (520 mg; 95%).

ii) Methane sulphonyl chloride (0.11 ml; 1.41 mmole) was added dropwise to an ice cold stirred solution of the above product (500 mg; 0.67 mmole) and N-methylmorpholine (0.16 ml; 1.4 mmole) in dry methylene chloride (15 ml). After three hours more methane sulphonyl chloride (0.03 ml) and N-methylmorpholine (0.04 ml) were added and the mixture kept at 0° C. overnight. The mixture was then washed in succession with water, saturated aqueous sodium bicarbonate and water, dried over MgSO$_4$ and evaporated to give the crude product which was chromatographed on silica gel. Elution with increasing proportions of ethyl acetate in hexane (4:6 to 1:9) gave the required methanesulphonyl derivative as a colourless foam (460 mg; 87%). Rf. 0.15 (ethylacetate, hexane, 1:1).

iii) Treatment of the above product (440 mg; 0.56 mmole) with trifluoroacetic acid as described in Example 39, followed by hydrolysis with 1N sodium hydroxide (4.5 ml) at 50°–55° C. for 65 hours and adsorption on ion-exchange resin 50W-X8 eluting with 10% aqueous pyridine gave the required diacid as a foam. Trituration with acetonitrile afforded a white powder (245 mg; 73%).

Found: C,54.92; H,8.29; N,9.12. C$_{28}$H$_{50}$N$_4$O$_8$S (0.5 H$_2$O) requires C,54.97; H,8.40; N,9.16%.

EXAMPLE 136

2-(N²-Methanesulphonyl-L-lysyl-aminomethyl)-3-{1-[(cis-4-carboxy-cis-3-(3-methylbutyl)-cyclohexyl)carbamoyl]cyclopentyl}propanoic acid This compound was prepared following the procedure of Example 135 but using c-4-amino-c-2-(3-methylbutyl)-r-1-cyclohexane carboxylic acid in step 3. The product was obtained as a cream powder. Found: C,56.07; H,8.22; N,8.95. C$_{29}$H$_{52}$N$_4$O$_8$S requires C,56.47; H,8.50; N,9.08%.

Preparation 1

3-{1-[(cis-4-Ethoxycarbonyl-cyclohexyl)carbamoyl]cyclopentyl}-2-(aminomethyl)propanoic acid t-butyl ester (a) A solution of 2-(bromomethyl)propenoic acid t-butyl ester (20 g, 90.5 mmole) in dry acetonitrile (360 ml), cooled to 0° C., was treated with solid potassium carbonate (15.63 g, 113 mmole), followed by a solution of dibenzylamine (17.83 g, 90.5 mmole), in dry acetonitrile (600 ml), producing a 10° C. exotherm. The reaction was stirred at 0° C. for 0.5 hours, followed by 1 hour at room temperature, and then partitioned between water and diethyl ether. The ether phase was washed again with water, dried (sodium sulphate) and evaporated to yield the crude product (31 g) which was filtered through a pad of silica, eluting with hexane/CH$_2$Cl$_2$ (1:1), to yield 2-(dibenzylaminomethyl)-propenoic acid t-butyl ester (23.8 g, 78%) as a solid, m.p. 62°–63° C. Found: C,78.09; H,8.20; N,4.18. C$_{22}$H$_{27}$NO$_2$ requires C,78.3; N,8.06; N,4.15%.

(b) To a stirred solution of diisopropylamine (14.98 g, 20.75 ml, 148 mmole) in dry tetrahydrofuran (250 ml) cooled to −30° C. under nitrogen, was added dropwise, n-butyl lithium (59.3 ml of a 2.5M solution, 148 mmole), keeping the temperature below −20° C. The reaction was stirred at −20° C. for 1 hour, then cooled to −30° C. and cyclopentanecarboxylic acid (8.05 g, 7.65 ml, 70.6 mmole) added dropwise in a small amount of dry tetrahydrofuran. The reaction mixture was stirred at 0° C. for two hours, during which time a white precipitate formed. The solution was then cooled to −70° C., and a solution of 2-(dibenzylaminomethyl)-propenoic acid t-butyl ester (23.8 g, 70.6 mmol) in dry tetrahydrofuran (35 ml) was added dropwise. The reaction was left overnight (below −40° C.), and then poured into iced hydrochloric acid (4.2 eq, final pH=2) and the product extracted into diethyl ether. The ether layer was washed with hydrochloric acid, water (2x), dried ($Na_2SO_4$) and evaporated to yield the crude product (40 g). This was chromatographed over silica gel (500 g) eluting with dichloromethane containing methanol (0 to 5%) to yield, on evaporation of the pure fractions, 3-(1-carboxycyclopentyl)-2-(dibenzylaminomethyl)-propanoic acid t-butyl ester as an oil (18.3 g, 57%). Found: C,74.38; H,8.41; N,2.91. $C_{28}H_{37}NO_4$ requires C,74.47; H,8.26; N,3.10%.

(c) The t-butyl ester from step (b) above (11.97 g, 26.54 mmole) in dry dichloromethane (200 ml), under nitrogen, was treated with 1-ethyl-3-(3-dimethylaminopropyl)carbodiimide hydrochloride (10.19 g, 53 mmole), 1-hydroxybenztriazole (3.94 g, 29 mmole), triethylamine (16.08 g, 22.15 ml, 159 mmole) and cis-4-aminocyclohexane-carboxylic acid ethyl ester hydrochloride (6.04 g, 20 mmole). After stirring overnight at room temperature, the solvent was evaporated and the residue partitioned between ethyl acetate and water. The organic phase was washed with dilute hydrochloric acid (2x), dilute aqueous sodium bicarbonate, water, dried ($Na_2SO_4$) and evaporated to yield the crude product (15.5 g). This was chromatographed on silica (400 g) eluting with 1 to 10% diethyl ether in dichloromethane. Evaporation of the desired fractions gave 3-{1-[(cis-4-ethoxycarbonyl-cyclohexyl)-carbamoyl]cyclopentyl}-2-(dibenzylaminomethyl)propanoic acid t-butyl ester as an oil (11.43 g, 71%). Found: C,73.38; H,8.87; N,4.42. $C_{37}H_{52}N_2O_5$ requires: C,73.48; H,8.67; N,4.68%.

(d) The product from step (c) above (4.6 g, 7.62 mmole) in ethanol (75 ml) was hydrogenated in an atmosphere of hydrogen (50 p.s.i., 3.46 bar) over palladium on charcoal (200 mg), at room temperature overnight. The reaction mixture was filtered through a Solkaflok pad, and the filtrate evaporated to dryness to yield the crude product as an oil. This was dissolved in diethyl ether, and extracted into dilute hydrochloric acid (pH 2) (2x). The combined aqueous layers were washed with diethyl ether, then neutralised with saturated aqueous sodium bicarbonate and extracted with dichloromethane (3x). The combined organic phases were dried ($Na_2SO_4$) and evaporated to yield the title amine as an oil (2.91 g, 90%). Found: C,64.80; H,9.28; N,6.76. $C_{23}H_{40}N_2O_5$ requires C,65.06; H,9.50; N,6.60%.

Preparations 2-6

The following compounds were prepared following the procedure of Preparation 1 but using the appropriate amino-cycloalkane carboxylic acid ester in step (c) instead of cis-4-aminocyclohexane-carboxylic acid ethyl ester.

| Preparation | B | Analysis % (Theoretical in brackets) | | |
|---|---|---|---|---|
| | | C | H | N |
| 2 | $CO_2C_2H_5$ (cyclohexyl) | 60.46 (61.88 | 9.11 9.05 | 6.09 6.19) |
| 3 | $(CH_2)_3CH_3$, $CO_2CH_3$ (cyclopentyl) | 66.34 (66.28 | 10.02 9.95 | 5.67 5.95)[1] |
| 4 | $CO_2C_2H_5$, $(CH_2)_3CH_3$ (cyclohexyl) | gum Rf 0.69 (silica; $CH_2Cl_2$, $CH_3OH$. $CH_3CO_2H$, 90:10:1) | | |
| 5 | $(CH_2)_3CH_3$, $CO_2C_2H_5$ (cyclohexyl) | 67.10 (67.46 | 10.09 10.06 | 5.69 5.83) |
| 6 | $(CH_2)_3CH_3$, $CO_2C_2H_5$ (cyclohexyl) | 67.07 (67.46 | 10.06 10.06 | 5.71 5.83) |

[1] 0.25 mole $H_2O$

We claim:
1. A compound having the formula:

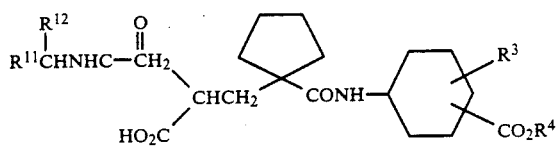

wherein
$R^3$ and $R^4$ are each independently hydrogen or $C_1$-$C_6$alkyl;
$R^{11}$ is hydrogen, benzyl, $C_1$-$C_6$alkyl, or $C_1$-$C_6$alkyl substituted by amino or benzyloxycarbonylamino;
$R^{12}$ is $COOR^9$ or $CONR^{13}R^{14}$;
$R^9$ is hydrogen, $C_1$-$C_6$alkyl, $C_3$-$C_7$cycloalkyl, phenyl or benzyl; and
$R^{13}$ and $R^{14}$ are each independently hydrogen, $C_1$-$C_6$alkyl, phenyl, or benzyl;
or a pharmaceutically acceptable salt thereof.
2. A compound of claim 1 wherein $R^3$ is hydrogen.
3. A compound of claim 2 wherein $R^4$ is hydrogen.
4. The compound of claim 3 wherein $R^{11}$ is benzyl, $R^{12}$ is $COOR^9$ and $R^9$ is hydrogen.

5. The compound of claim 3 wherein $R^{11}$ is 4-(benzyloxycarbonylamino)butyl, $R^{12}$ is $CONR^{13}R^{14}$ and $R^{13}$ and $R^{14}$ are each methyl.

6. A compound of claim 2 wherein $R^4$ is ethyl.

7. A compound of claim 6 wherein $R^{11}$ is 4-(benzyloxycarbonylamino)butyl and $R^{12}$ is $CONR^{13}R^{14}$.

8. The compound of claim 7 wherein $R^{13}$ and $R^{14}$ are each methyl.

9. A pharmaceutical composition for administration to a mammal in the treatment of cardiovascular disorders which are mediated by atrial natriuretic factor comprising a zinc-dependent, neutral endopeptidase inhibiting amount of a compound of claim 7 together with a pharmaceutically acceptable diluent or carrier.

10. A method for inhibiting zinc-dependent, neutral endopeptidase in the treatment of cardiovascular disorders which are mediated by atrial natriuretic factor in a mammal which comprises administering to said mammal a zinc-dependent, neutral endopeptidase inhibiting amount of a compound of claim 1.

* * * * *